US008893719B2

(12) United States Patent
Lavi et al.

(10) Patent No.: US 8,893,719 B2
(45) Date of Patent: Nov. 25, 2014

(54) INTRA-ORAL CONTINUOUS POSITIVE AIRWAY PRESSURE (CPAP) INTERFACES

(75) Inventors: Eran Lavi, Givatayim (IL); David Madjar, Ramat Gan (IL)

(73) Assignee: Discover Medical Devices Ltd., Tel Aviv (IL)

( * ) Notice: Subject to any disclaimer, the term of this patent is extended or adjusted under 35 U.S.C. 154(b) by 614 days.

(21) Appl. No.: 13/203,982

(22) PCT Filed: Feb. 24, 2010

(86) PCT No.: PCT/IL2010/000157
§ 371 (c)(1),
(2), (4) Date: Aug. 31, 2011

(87) PCT Pub. No.: WO2010/100639
PCT Pub. Date: Sep. 10, 2010

(65) Prior Publication Data
US 2011/0315141 A1 Dec. 29, 2011

Related U.S. Application Data

(60) Provisional application No. 61/272,889, filed on Nov. 16, 2009.

(30) Foreign Application Priority Data

Mar. 1, 2009 (IL) .......................................... 197330

(51) Int. Cl.
*A62B 9/06* (2006.01)
(Continued)

(52) U.S. Cl.
CPC ....... *A61M 16/0816* (2013.01); *A61M 16/0683* (2013.01); *A61M 16/0488* (2013.01); *A61M 2210/0625* (2013.01); *A61M 16/049* (2013.01)
USPC ............. 128/206.29; 128/200.26; 128/207.14

(58) Field of Classification Search
CPC ............ A61M 16/04; A61M 16/0048; A61M 16/0488; A61M 2016/0493; A61M 16/049; A02B 9/06
USPC ............. 128/200.26, 206.29, 207.14, 207.15, 128/848, 859–862; 433/34, 37, 38; 600/242
See application file for complete search history.

(56) References Cited

U.S. PATENT DOCUMENTS 1,483,694 A * 2/1924 Stukey .......................... 128/859
2,627,268 A * 2/1953 Leppich ........................ 128/848

(Continued)

FOREIGN PATENT DOCUMENTS

JP S58180165 A 10/1983

OTHER PUBLICATIONS

Notification of Reasons for Rejection parallel Japan Application 2011-551566 issued Feb. 4, 2014 by Japanese Patent Office.

(Continued)

*Primary Examiner* — Jackie T Ho
*Assistant Examiner* — Kathryn E Ditmer
(74) *Attorney, Agent, or Firm* — Simon Kahn; Chanoch Kahn

(57) ABSTRACT

The present invention provides intra-oral interfaces, systems and methods for preventing sleep apnea, the interfaces comprises a conduit adapted to receive continuous positive airway pressure (CPAP) from a CPAP source, and for delivering positive air pressure to a mouth of a patient, a mouthpiece through which the conduit extends, the mouthpiece having a portion configured to reside between the teeth and inner part of the lips and cheeks in the mouth of the patient; and an active seal associated with the mouthpiece, the active seal having at least a portion thereof adapted to reside in a buccal vestibulum of the patient, the active seal being configured to bulge and contract as the patient breathes.

19 Claims, 13 Drawing Sheets

(51) Int. Cl.
*A62B 18/08* (2006.01)
*A61M 16/00* (2006.01)
*A61M 16/04* (2006.01)
*A61M 16/08* (2006.01)
*A61M 16/06* (2006.01)

(56) References Cited

U.S. PATENT DOCUMENTS

| | | | | |
|---|---|---|---|---|
| 2,857,911 | A | * | 10/1958 | Bennett ............... 128/206.24 |
| 2,867,212 | A | * | 1/1959 | Nunn, Jr. ................ 128/848 |
| 4,305,387 | A | * | 12/1981 | Reist-Kundig et al. .. 128/202.28 |
| 4,495,945 | A | | 1/1985 | Liegner |
| 4,881,540 | A | * | 11/1989 | Vigilia ............... 128/202.28 |
| 5,638,811 | A | * | 6/1997 | David ................ 128/207.14 |
| 5,950,624 | A | | 9/1999 | Hart |
| 6,076,526 | A | * | 6/2000 | Abdelmessih ........... 128/848 |
| 6,263,877 | B1 | * | 7/2001 | Gall ..................... 128/848 |
| 6,820,617 | B2 | | 11/2004 | Robertson et al. |
| 6,966,319 | B2 | * | 11/2005 | Fitton .................... 128/848 |
| 2002/0104541 | A1 | | 8/2002 | Bibi et al. |
| 2003/0089371 | A1 | | 5/2003 | Robertson |
| 2005/0166929 | A1 | | 8/2005 | Jiang |
| 2006/0081249 | A1 | | 4/2006 | Duxbury |
| 2007/0049841 | A1 | | 3/2007 | Lepel |
| 2008/0046022 | A1 | | 2/2008 | Bhat et al. |

OTHER PUBLICATIONS

First Office Action for Parallel Application CN201080018653.2 mailed Jan. 6, 2013.
Second Office Action from Chinese Patent Office for parallel application CN 201080018653.2 mailed Jun. 5, 2013.
Amended Claim set in response to first office action of Chinese patent office for parallel application CN 201080018653.2 filed May 17, 2013.
Arguments in response to first office action of Chinese patent office for parallel application CN 201080018653.2 filed May 17, 2013.
Beecroft et al. 'Oral Continuous Positive Airway Pressure for Sleep Apnea: Effectiveness, Patient Preference and Adherence' Chest 124:2200-2208 (2003) Abstract; p. 2202, col. 2, para 1; p. 2203, col. 1. para 1.
Office Action dated Jul. 19, 2013 for U.S. Appl. No. 13/497,072.

* cited by examiner

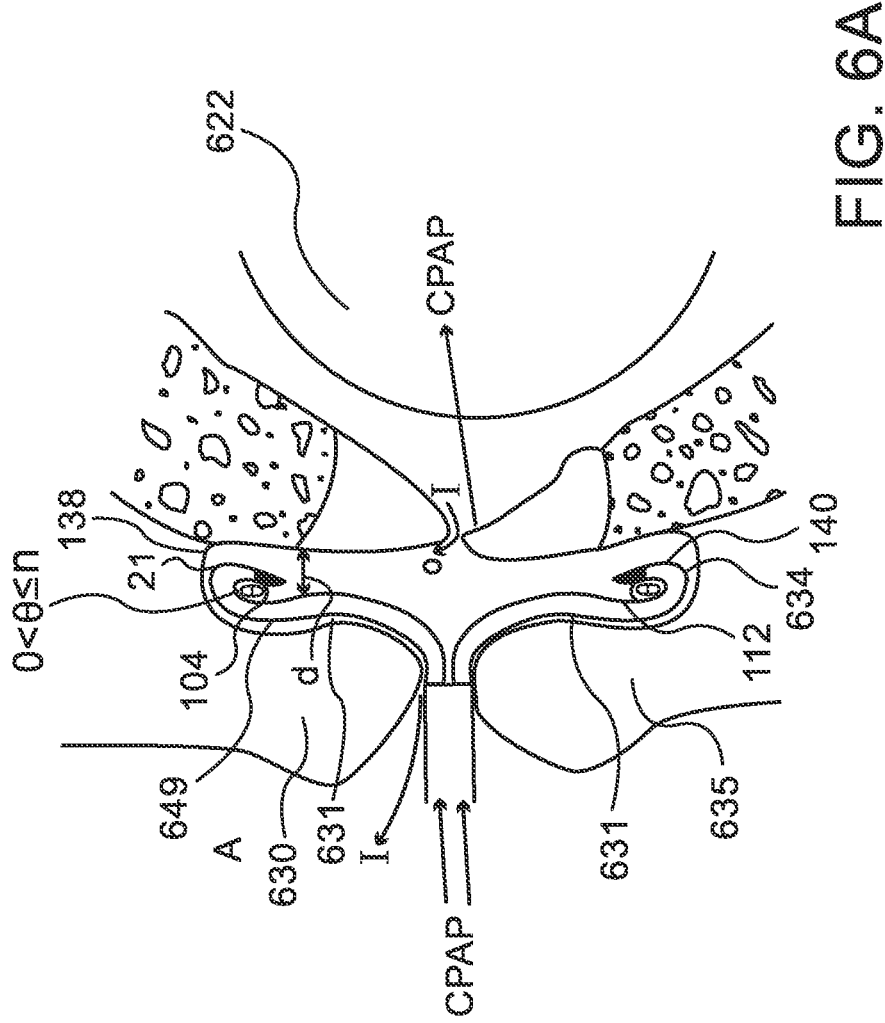

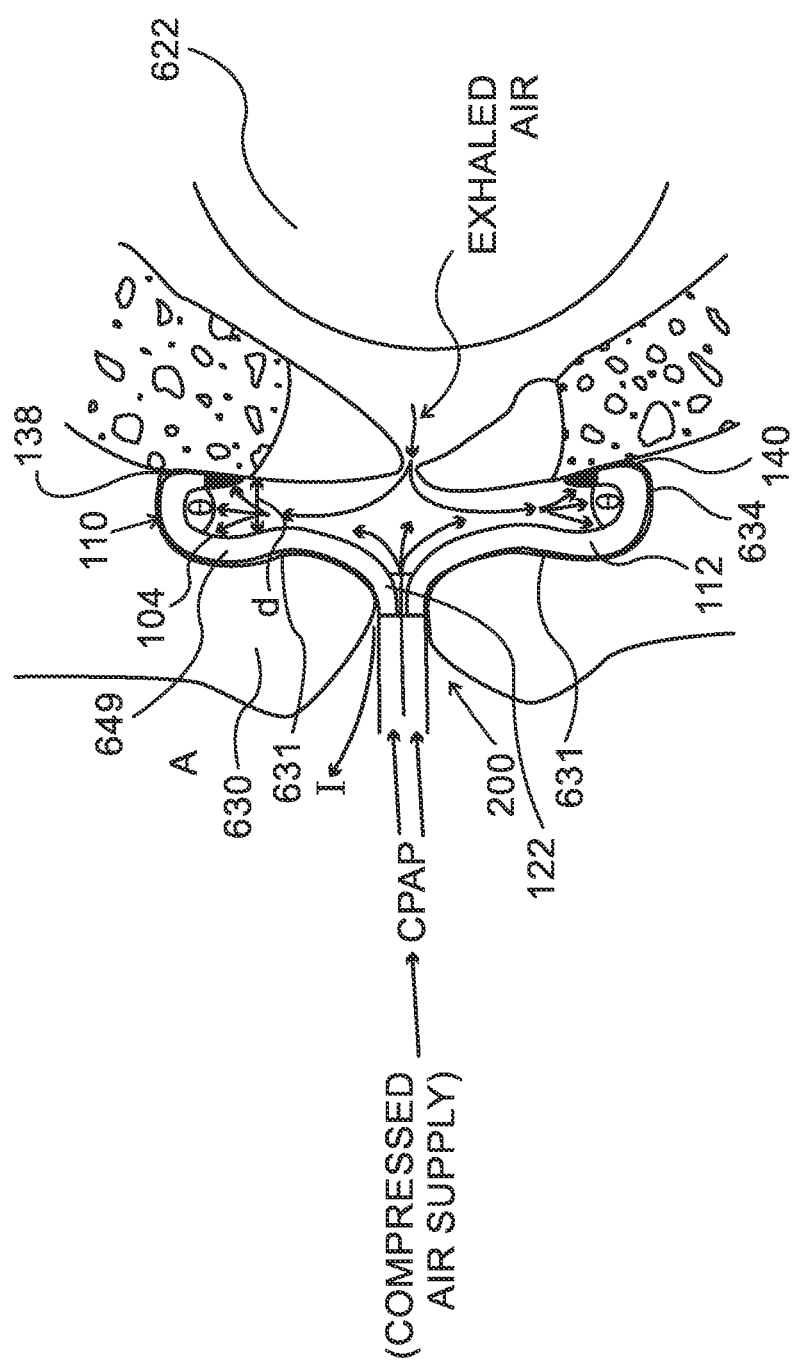

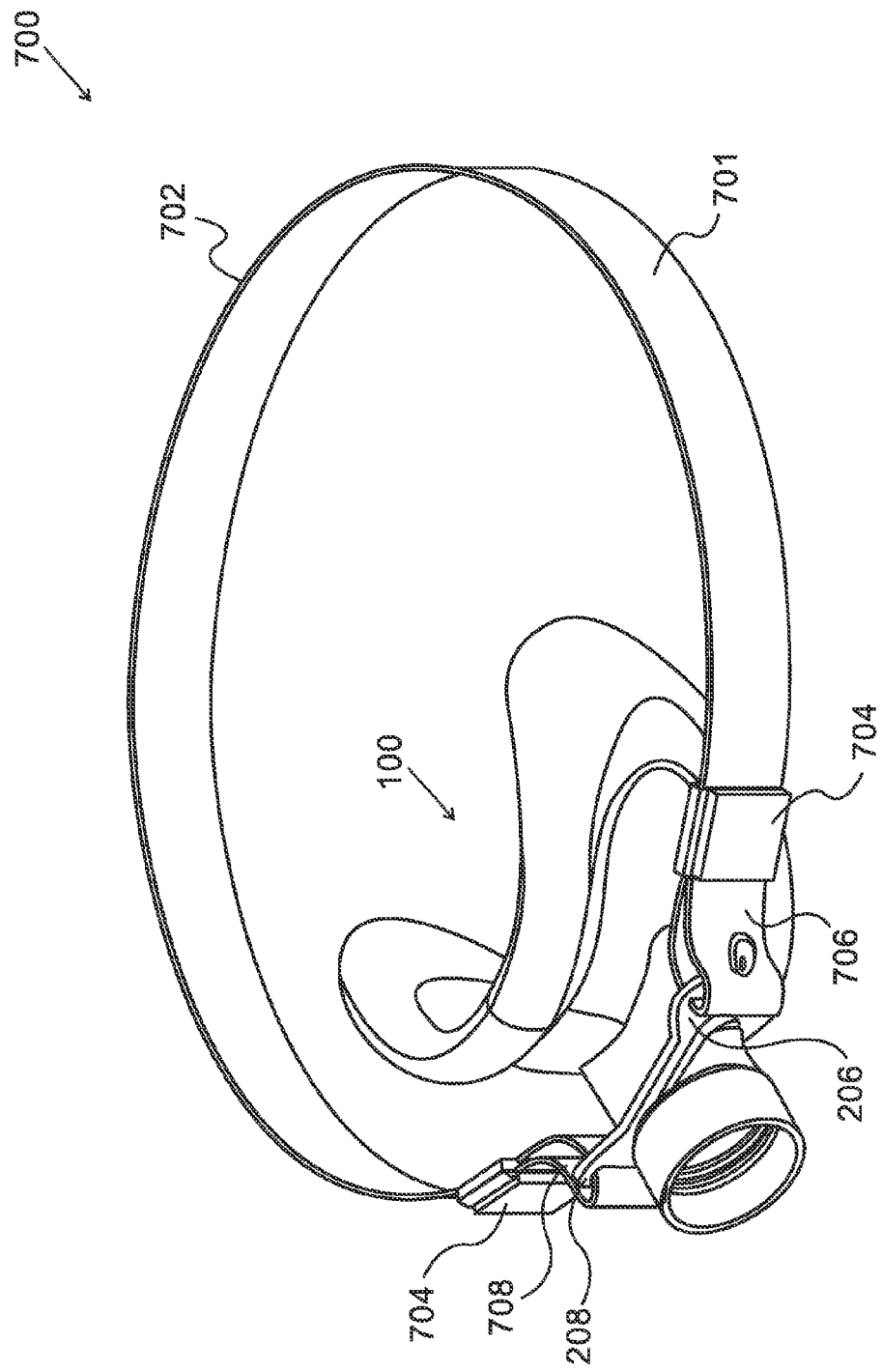

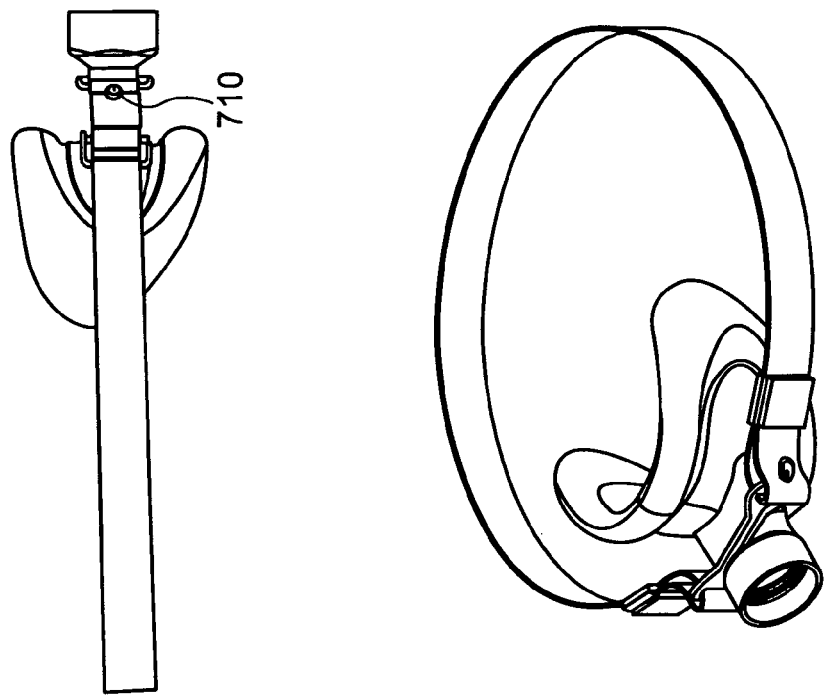
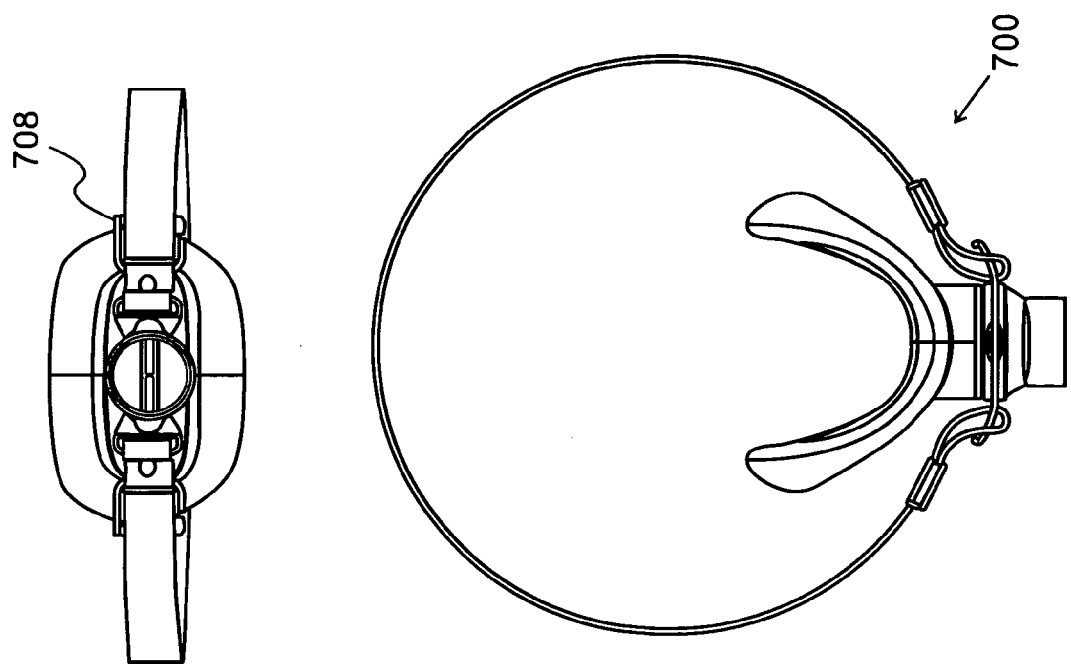
FIG. 7B

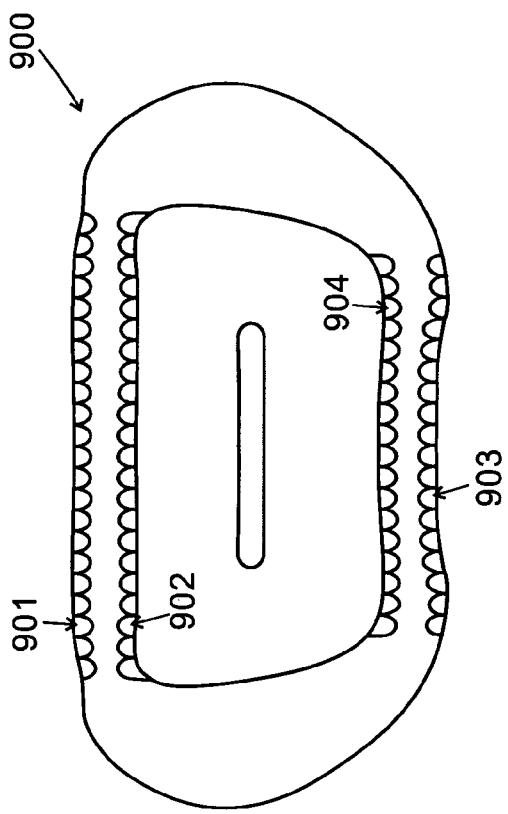
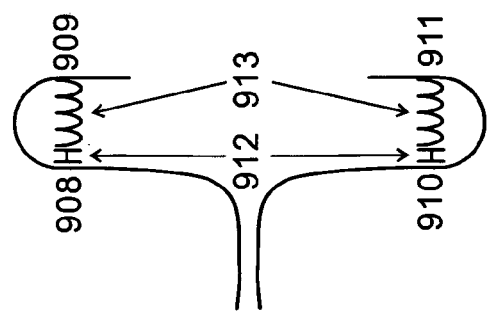
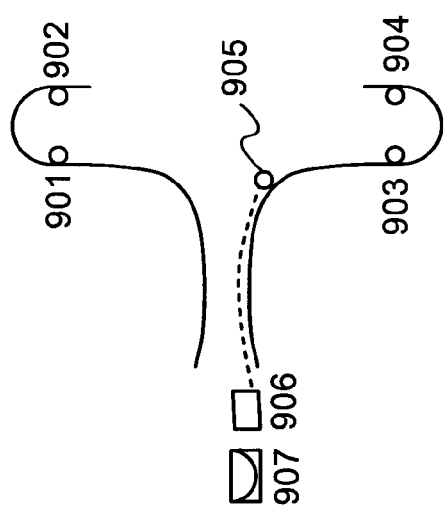
FIG. 9

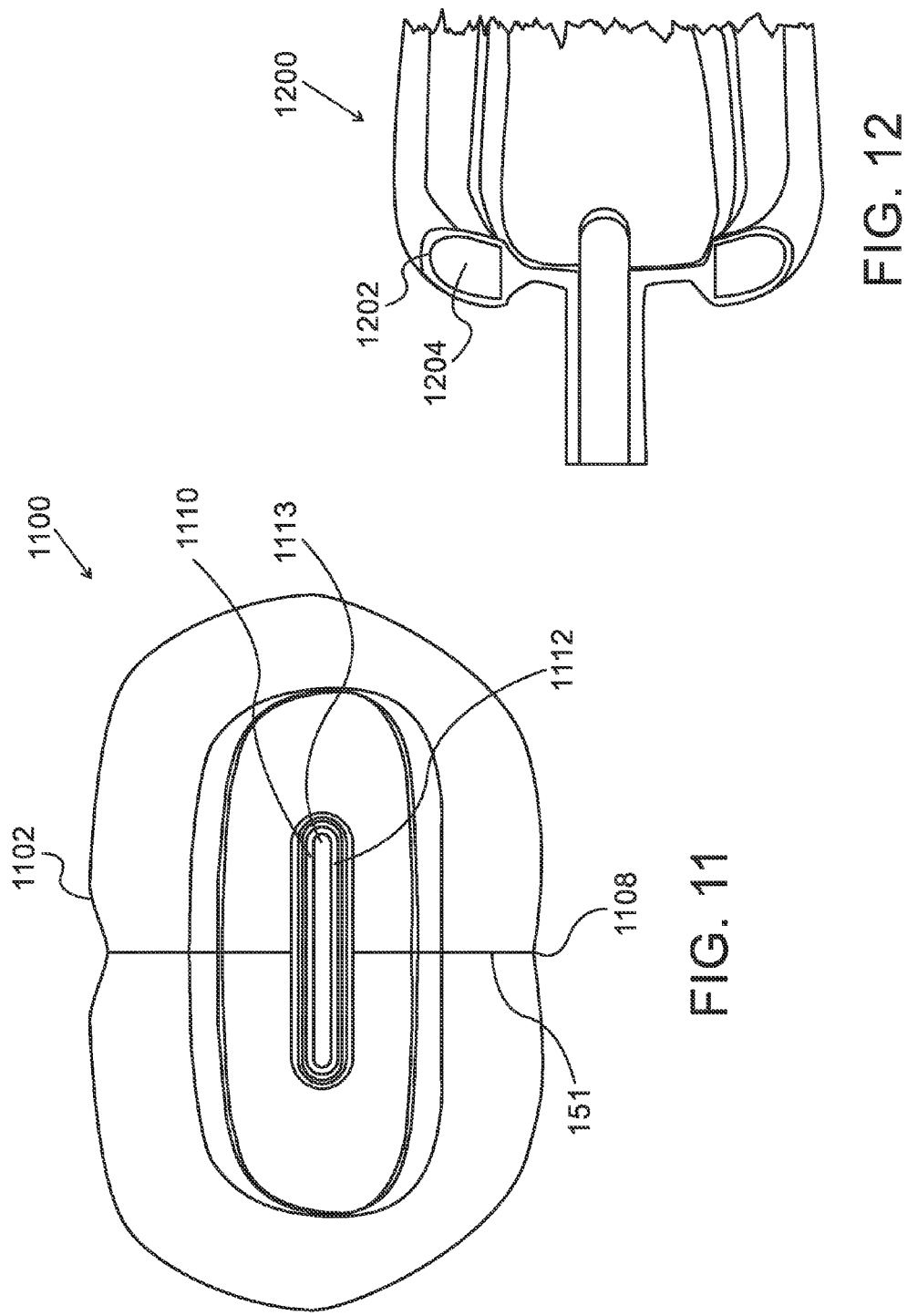

INTRA-ORAL CONTINUOUS POSITIVE AIRWAY PRESSURE (CPAP) INTERFACES

CROSS-REFERENCE TO RELATED APPLICATIONS

The current application is a U.S. National Phase Application under 35 U.S.C. 371 of PCT International Application No. PCT/IL2010/000157, which has an international filing date of Feb. 24, 2010, and which claims the benefit of priority from Israel Patent Application No. 197,330, filed Mar. 1, 2009, and U.S. Provisional Patent Application No. 61/272,889, filed Nov. 16, 2009, the disclosures of which applications are incorporated herein by reference in their entirety

FIELD OF THE INVENTION

The present invention relates generally to apparatus and methods for providing gases intra-orally, and more specifically to ergonomic apparatus and methods for providing continuous positive air pressure to a mammalian subject.

BACKGROUND OF THE INVENTION

Mammalian subjects require a semi-continuous supply of air, such that the oxygen level in the brain is retained above a threshold level. There are many conditions and situations under which the air supply is temporarily stopped or reduced. These may include, but are not limited to, sleep apnea, heart attack, epileptic seizure and drowning. If the subject does not receive oxygen within a number of seconds/minutes, the result can lead to irreversible brain damage, and, in some cases, death.

Many devices and methods have been developed to ensure a continuous air supply to human subjects. However, many of the devices are cumbersome, uncomfortable and lead to patient non-compliance. Other devices are not adapted to deal with patient movement.

Some publications in the field include U.S. Pat. No. 4,305,387, which describes a mouth closure for providing artificial respiration to patients, which consists of a deformable elliptical plate, whose periphery is surrounded by a tube. The tube is formed in the shape of an air hose made of an elastic film with a hose for admission of air. A tube passes through the plate in a central region. The mouth closure is placed in the dentilabial cavity of the patient's upper and lower jaws. The tube, in association with the gums and the lips and cheeks, seals the oral cavity from the outside. A flow of air through the tube therefore enters the respiratory passages of the patient and also passes back from the respiratory passages, through the tube, to the outside. This publication teaches the requirement for a medical professional to fill the airholes, thereby preventing a user from using it just by itself. This device is not self-adaptable.

US Patent Publication No. US2002005201 describes an improved nasal mask, for delivering CPAP therapy to patients. The nasal mask has a sliding engagement to the headgear. The sliding engagement allows substantial relative lateral movement eg: when face is distorted from sleeping on side, while still providing adequate compressive force to avoid side leakage. The sliding engagement also allows easy release from the headgear.

US Patent Publication No. US2003075182 discloses an application device for a breathing mask arrangement, including a base portion, a holding portion structured to support a mask and pivotally mounted to the base portion for pivotal movement about a first pivot axis, a right arm element pivotally mounted to the base portion for pivotal movement about a second pivot axis, and a left arm element pivotally mounted to the base portion for pivotal movement about a third pivot axis. The right and left arm elements are each provided with a contact portion for bearing against a right and a left forehead zone respectively of a mask user. The holding portion, the right arm element, and left arm element can be pivoted with respect to the base portion about the respective first, second, and third pivot axes.

US Patent Publication No. US2003183227 describes a CPAP device and a method for treating sleep apnea, using a head appliance with an oral adaptor comprising a tube partially inserted in a person's mouth and a diaphragm applied over the tube against the mouth, such that the lips are formed into a tight seal with the tube. A nasal seal is described comprising two rollers to which a strap is attached, so that the nasal seal is easily put in place, adjusted and maintained by rolling the rollers on the nose sides or pulling the straps.

US Patent Publication No. US2003089371A describes a mouthpiece for oral delivery of CPAP treatment, which has a vestibular shield for location between the teeth and lips/cheeks of a wearer. The vestibular shield is dimensioned to extend laterally into the buccal vestibule and vertically to overlap the gums. The vestibular shield is formed from a very supple material. A gases pathway is provided through the vestibular shield and may include a hard plastic insert through the shield, including a standard breathing conduit connection at its outer end. A short stub conduit on the outlet side of the shield passes between the wearers upper and lower teeth. A connection for connecting the mouthpiece to a breathing circuit is also provided which reduces the transfer of forces caused by movement therebetween. The connection may include a short length of highly flexible gases conduit, an elbow and a swivel connection.

US Patent Publication No. US2005236003A describes a sleep apnea prevention device which is designed to move the lower jaw forward, keep teeth and lips apart, and guarantee full oxygenation needs with oral airway that is centered in an anterior dental-buccal space shield and wing portion. This, with mouth guard for lower teeth, is all a unit as a single piece of molded plastic or any other material; with said unit modeled from four theoretical portions including a barrier-like anterior portion fitted and anchored between anterior teeth-gums and behind the lips in the anterior buccal space with flanking wing like fins extending in that space laterally back to the upper second molars, thus allowing good retention in place whether mouth is open wide or minimally, or closed or moving side to side. Said shield is functionally tethered at the top front which becomes its fulcrum as it engages the lower teeth with a mouth guard portion and swings the lower jaw forward with bite activity; mouth guard pylon like blocks mounted on the mouth guard superior surface keep the teeth apart and help swing the jaw forward. The barrier in midline supports a nipple like projection which is, actually, a tube-like conduit which keeps the lips apart and becomes an oral airway. This device can be used alone or with CPAP face mask in place and user must coordinate with health provider to insure sleep apnea is only moderate and not just masked and inadequately treated. It usually does help snoring and bruxism.

World Patent Publication No. WO06079149A discloses an oral leak prevention device for patients who use nasal CPAP machines (Continuous positive airway pressure). The device minimizes air escaping through the mouth of patient while they are being pressurized through the nasal passage by the airflow of a CPAP machine. The oral leak prevention device is placed over the mouth and securing straps hold the device in place. The built in valve is to allow the patient to inhale if the CPAP machine should fail but under normal circumstances the valve stops air escaping from the mouth while the patient is sleeping.

US Patent Publication No. US2007131229A relates to a respiratory mask arrangement that can be used in the framework of CPAP therapy for treating sleep-related disturbances, for example. In one embodiment a respiratory mask arrangement comprises a sealing lip device to be placed on the facial surface of a mask user, a covering device which defines a mask interior in cooperation with the sealing lip device, and a respiratory gas conduit unit for delivering respiratory gas to the mask interior that is defined by the covering device and is connected to the nostril and/or oral opening of the mask user. At least some sections of the covering device are embodied as an air-permeable structure.

World Patent Publication No. WO08041237A describes an intra-oral continuous positive airway pressure (CPAP) device that comprises a tube connected to a source of positive air pressure, and a shield connected to, or integrally formed with, the tube and adapted to be inserted within buccal sulci in such a way that facilitates oral cavity sealing. The shield has a central part formed with an aperture in communication with the tube, and right and left longitudinally extending projections adjoining, and of substantial bilateral symmetry with respect to the central part. Each of the projections has adjoining upper and lower regions and each of the regions has adjoining proximal and distal portions, Each of the projections is dimensioned such that a distal portion has a thickness substantially equal to, or greater than, a buccal sulcus potential space gap, and is configured, when inserted within a buccal sulcus, in such a way so as to adhere to the oral mucosa, to occupy the entire volume of buccal sulcus potential space, and to seal the oral cavity.

Despite the advances of the inventions described hereinabove, there is still a need to provide CPAP devices and methods which are less cumbersome and of better ergonomics, thereby providing devices which lend themselves to greater patient compliance.

SUMMARY OF THE INVENTION

It is an object of some aspects of the present invention to provide interfaces and methods for providing air to patients to prevent their death and injury due to a temporary stoppage of their natural breathing process.

It is an object of some aspects of the present invention to provide interfaces and methods for providing air to patients to prevent their death and injury due to a reduction of air intake during their natural breathing process.

In preferred embodiments of the present invention, improved methods and apparatus are provided for preventing death and injury in patients suffering from sleep apnea, stroke, heart attack, trauma, COPD, Alzheimer and other conditions.

In other preferred embodiments of the present invention, a method and an intra-oral interface for providing continuous positive airway pressure (CPAP) to a patient.

In additional preferred embodiments for the present invention, an intraoral interface is provided which is non-obtrusive, comfortable, does not impinge on or touch the soft palate, tongue or teeth. The interface is simple to use, lightweight and ergonomically designed.

In additional preferred embodiments for the present invention, an ergonomically formed intra-oral interface is provided for providing an unconscious, semi-conscious or sleeping patient with continuous positive airway pressure (CPAP).

In further preferred embodiments of the present invention, an interface provides for continuous positive airway pressure (CPAP) maintenance in a patient.

In further preferred embodiments of the present invention, an interface provides for non invasive ventilation in a patient.

There is thus provided according to some embodiments of the present invention, an intra-oral continuous positive airway pressure (CPAP) interface, including;
 a) a hollowed ellipsoid tube section open towards the teeth;
 b) a central section in communication with a source of positive air pressure at a first end of the hollowed ellipsoid tube;
 c) an intra-oral section extending perpendicularly from a second end of the hollowed ellipsoid tube section, the intra-oral section including;
  i. a buccal hollowed ellipsoid surface; and
  ii. a lingual rim projecting from a circumferential border of the hollowed ellipsoid surface thereby forming a circumferential hollow lip, wherein the hollow lip is adapted to bulge upon receiving air, thereby forming a circumferential air pocket within the circumferential hollow lip.

Additionally, according to some embodiments of the present invention, the intra-oral section is adapted to be inserted within buccal sulci occupying substantially the entire volume of a buccal sulcus potential space upon receiving air in such a way that facilitates oral cavity sealing, and to retain oral cavity sealing in a sealed state even without occupying the entire volume of a buccal sulcus potential space.

According to some embodiments, the interface is lightweight. Preferably, the interface weighs less than 60 grams. Yet more preferably, the interface weighs 20 to 50 grams.

Additionally, according to some embodiments of the present invention, the interface is non-obtrusive.

Furthermore, according to some embodiments of the present invention, the interface is constructed and configured to conform to mouth physiology of a patient.

Additionally, according to some embodiments of the present invention, the interface is constructed and configured to be self-adaptable to a physical intra-oral structure of every individual user.

Self-adaptable are active and passive interface features that allow it to automatically fit to different oral anatomy structures, sizes and functions.

Yet further, according to some embodiments of the present invention, the interface is constructed and configured to passively form a seal by occupying a potential space between the lips and gums of a user.

Additionally, according to some embodiments of the present invention, the interface is constructed and configured to actively seal a potential space between the lips and gums of a user.

According to some embodiments, the circumferential hollow lip is adapted to be inflated by exhaled air of the user.

Additionally, according to some embodiments of the present invention, the interface is made of a biocompatible polymer.

Additionally, according to some embodiments of the present invention, the polymer of the circumferential hollow lip includes collapsible portions.

Furthermore, according to some embodiments of the present invention, the collapsible portions exhibit a pre-loaded force which is adapted to press gently onto the gums and lips of the user upon insertion to a mouth of the user, thereby forming a seal.

Additionally, according to some embodiments of the present invention, the orifice intra-oral section is integrally formed with the tubular section.

Yet further, according to some embodiments of the present invention, the intra-oral section is provided with a central part formed with an aperture in communication with the tube, and right and left longitudinally extending projections adjoining, and of substantial bilateral symmetry with respect to, the central part, each of the projections having adjoining upper and lower regions and each of the regions having adjoining proximal and distal portions, wherein each of the projections is dimensioned such that a distal portion has a thickness substantially equal to, or greater than, a buccal sulcus potential space gap, and is configured, when inserted within a buccal sulcus, in such a way so as to adhere to the oral mucosa, to occupy substantially the entire volume of buccal sulcus potential space, and to seal the oral cavity.

Additionally, according to some embodiments of the present invention, each of the projections is continuously adherable to the oral mucosa from the orbicularis oris muscle to the attached gingiva.

According to some embodiments, the intra-oral section has a longitudinal length equal to 10 to 16 teeth. In some cases, the intra-oral section has a longitudinal length equal to approximately 12 teeth.

Additionally, according to some embodiments of the present invention, a most distal location of a proximal portion and a transitional point between the orbicularis oris muscle and the buccinator muscle are approximately at a common height when the shield in inserted within the potential space of the buccal sulci.

Furthermore, according to some embodiments of the present invention, a distal portion may be considerably thicker than an adjoining proximal portion and than a corresponding distal portion of the buccal sulcus potential space to such a degree that upper and lower lip portions disposed buccally to the central part are urged to sealingly engage the tube.

There is thus provided according to some further embodiments of the present invention, an intra-oral CPAP interface constructed and configured to supply sufficient air to the patient at an air pressure of 2-20 cm $H_2O$. This is approximately 15-60% less air pressure than the requirements of interfaces known in the art for similar therapeutic results.

According to another embodiment of the present invention, the intra-oral (CPAP) interface is constructed and configured to supply sufficient air to the patient at an air pressure of 2-10 cm $H_2O$.

According to an additional embodiment of the present invention the interface is constructed and configured to supply sufficient air to the patient at an air pressure of 4-8 cm $H_2O$.

According to yet another embodiment of the present invention, the interface is constructed and configured to supply sufficient air to the patient at an air pressure reduced by 10-60% relative to an existing CPAP interface.

According to yet an additional of the present invention, the interface is constructed and configured to supply sufficient air to the patient at an air pressure reduced by 15-50% relative to an existing CPAP interface.

There is thus provided according to some additional embodiments of the present invention, an intra-oral interface, including;
 a) a hollowed ellipsoid tube section open towards the teeth;
 b) a hollow in the shape of an ellipsoid centered in the hollowed ellipsoid tube section open towards the teeth;
 c) an intra-oral section extending perpendicularly from the hollowed ellipsoid section, the intra-oral section including;
  i. a buccal hollowed ellipsoid surface; and
  ii. a lingual rim projecting from a circumferential border of the hollowed ellipsoid surface thereby forming a circumferential hollow lip.

There is thus provided according to some further embodiments of the present invention, an intra-oral interface that is not connected to a CPAP machine during CPAP treatment. The CPAP treatment is supplied via other nasal or ora-nasal interfaces and in such a case the air pressure needed for a successful therapy is reduced by 10-60% relative to an existing CPAP interface, while the intra oral interface in this embodiment support and augment the action of the existing CPAP interface.

There is thus provided according to some additional embodiments of the present invention, a system for continuously providing a user with sufficient air, the system including;
 a) a CPAP interface as described herein;
 b) at least one set of coils disposed in the interface;
 c) at least one sensor adapted to receive data from an interface neighborhood;
 d) a flow generator adapted to provide air to the CPAP interface; and
 e) a data processing unit constructed and configured to;
  1. process and store the data; and
  2. to provide signals responsive to the data to at least one of the coils and an air inlet controller.
  3. to provide signals responsive to the data or signals from the flow generator unit.

Furthermore, according to some embodiments of the present invention, the coils include fixed magnets pairs.

Additionally, according to some embodiments of the present invention, the signals are adapted to induce at least one of attraction and repulsion in the magnet pairs thereby decreasing or increasing the air volume in the interface.

Furthermore, according to some embodiments of the present invention, the sensors are adapted to measure at least one parameter selected from the group consisting of air pressure, air flow speed, oxygen saturation, carbon dioxide concentration, pulse rate and blood pressure.

Yet further, according to some embodiments of the present invention, the system is adapted to prevent at least one of sleep apnea, snoring and hypopnea.

Furthermore, according to some embodiments of the present invention, the sensor is selected from an integral pulse oximeter and a CO-oximeter.

According to further embodiments, the sensors transmit data and or processes data to the flow generator, which, in turn, uses the data and regulates the air is supplies and thus work in concert with the interface to provide a better therapeutic compliance to the patient's needs.

There is thus provided according to some further embodiments of the present invention, a method for forming an intra-oral CPAP interface including;
 a) press molding a biocompatible polymer in a mold to form a first surface having a rear rim projecting from a circumferential border thereof; and
 b) extruding an inner section thereof to form a hollow section extending perpendicularly from a front central section of the first surface, thereby forming the intra-oral CPAP interface.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified pictorial illustration of a perspective view of a CPAP (continuous positive air pressure) intra-oral self adaptable interface, in accordance with an embodiment of the present invention;

FIG. 2 is a simplified pictorial illustration of a rear view of the CPAP intra-oral interface of FIG. 1 in accordance with an embodiment of the present invention;

FIG. 3 is a simplified pictorial illustration of an upper view of a CPAP intra-oral interface of FIG. 1, in accordance with an embodiment of the present invention;

FIG. 4 is a simplified pictorial illustration of a front view of a CPAP intra-oral interface of FIG. 1, in accordance with an embodiment of the present invention;

FIG. 5 is a simplified flow chart of a method for forming a general purpose CPAP intra-oral interface, in accordance with an embodiment of the present invention;

FIG. 6A is a simplified pictorial illustration of a vertical cross section of the CPAP intra-oral interface of FIG. 1 with a CPAP flow generator during inhalation, in accordance with an embodiment of the present invention;

FIG. 6B is a simplified pictorial illustration of a vertical cross section of the CPAP intra-oral interface of FIG. 1 with air introduction from a CPAP flow generator, during exhalation, in accordance with an embodiment of the present invention;

FIG. 7A is a simplified pictorial illustration of a perspective view of a CPAP intra-oral interface of FIG. 1 with a retainer element, in accordance with an embodiment of the present invention;

FIG. 7B shows a number of views of the CPAP intra-oral interface with the retainer element of FIG. 7A, in accordance with an embodiment of the present invention;

FIG. 8 shows a number of views of another embodiment of a CPAP intra-oral interface, in accordance with an embodiment of the present invention;

FIG. 9 is a simplified pictorial illustration of a CPAP intra-oral interface comprising a set of pairs of coils designed to repulse each other, in accordance with an embodiment of the present invention;

Figure 10:
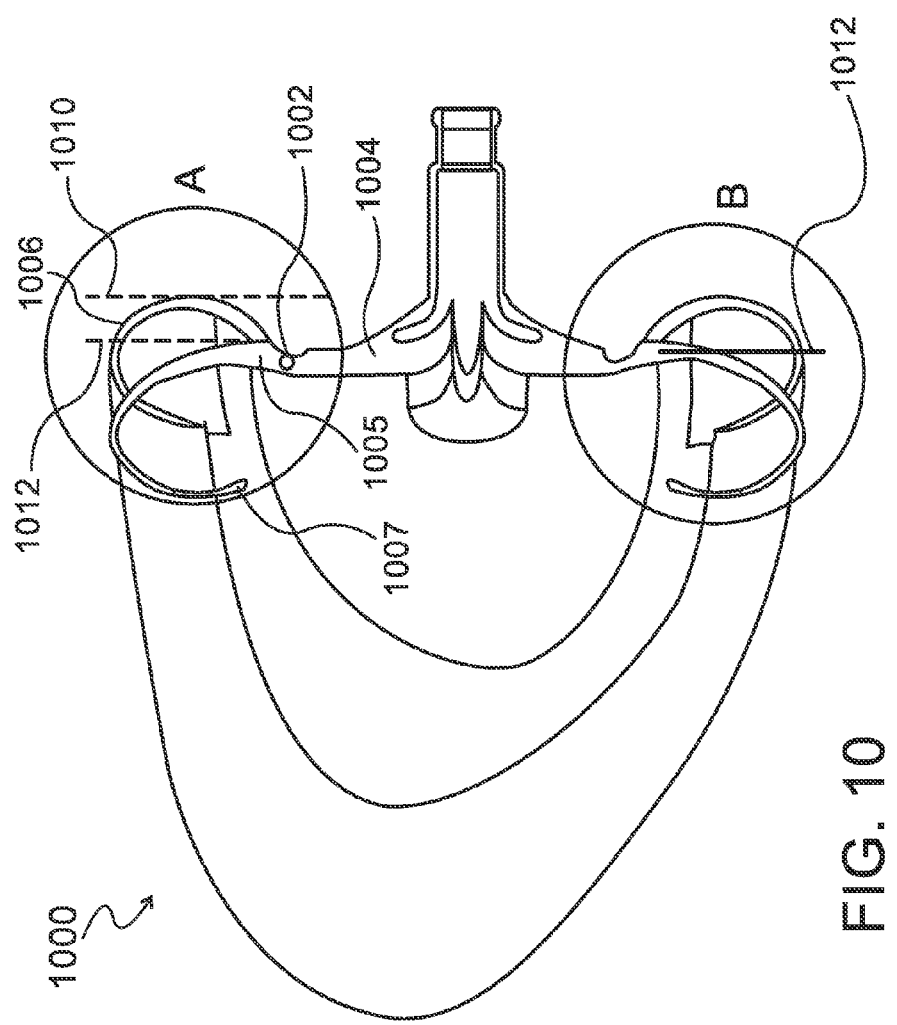

FIG. 10 is a simplified pictorial illustration of a CPAP intra-oral interface, in accordance with an embodiment of the present invention;

FIG. 11 is a simplified pictorial illustration of a rear view of a CPAP intra-oral interface, in accordance with an embodiment of the present invention; and FIG. 12 is a simplified pictorial illustration of a filled CPAP intra-oral interface, in accordance with an embodiment of the present invention;

In all the figures similar reference numerals identify similar parts.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

All terms used herein are in accordance with the definitions and teachings of World Patent Publication No. WO08041237, incorporated herein by reference. '237 teaches a shield, having a buccal portion substantially equal to, or greater than, a buccal sulcus potential space gap.

The present invention provides intra-oral interfaces for providing continuous positive airway pressure (CPAP) to a patient. Various designs of the hollowed interfaces, adapted to create air pockets within the interfaces are described herein, but should not be deemed as limiting.

Figure 1:
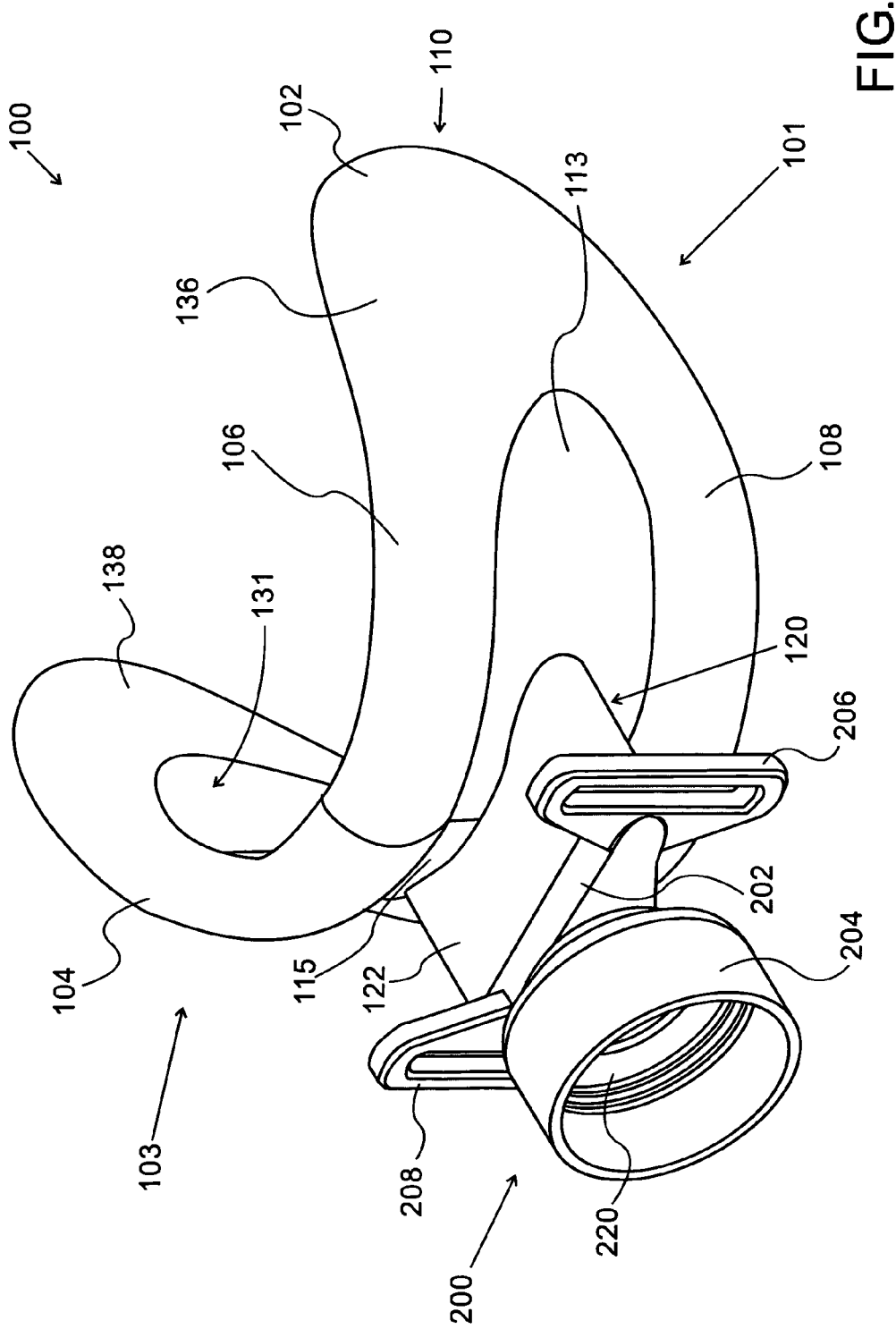

Reference is now made to FIG. 1, which is a simplified pictorial illustration of a perspective view of a CPAP intra-oral interface 100, in accordance with an embodiment of the present invention.

Device 100 comprises an intraoral hollowed ellipsoid tube section 120, and an intra-oral section 110, which serve as a barrier between the oral cavity and atmospheric pressure air. Section 110 in communication with the source of positive air pressure has left and right arcuate projections 101 and 103 of bilateral symmetry with respect to tube section 120. Projections 101 and 103 are configured to match the internal anatomy of a patient's mouth (see further discussion and Table 1 hereinbelow).

Tube section 120 is constructed and configured as a male portion to fit onto a female portion 202 of an adapter element 200. The tube section is made out of a biocompatible polymer and is shaped to conform to the mouth opening during rest. It is of a generally elliptical cross-section with flattened horizontal upper and lower sides 122. Adapter element 200 serves a number of functions, including, providing the female portion on which the tube section is mounted, in air-sealable tight fit; providing a hollowed round portion 204 of a suitable cross-section to ensure a suitable air flow rate for CPAP, thereby maintaining the patient's airway remains unobstructed; allowing hollowed ellipsoid portion to be engaged with an auxiliary tube (not shown) of a different orientation. The auxiliary tube may be used as a connector to a tube through which CPAP air flows from a CPAP flow generator, e.g. a compressor or air pump (not shown), to interface 100. According to some embodiments, hollowed rounded portion 204 is rotatable with respect to the auxiliary tube and vice versa, to advantageously afford the patient a large amount of mobility when asleep without concern that the supply of CPAP air will be disrupted. It should be understood that the interface of the present invention may be connected to a valve or interface which serves to prevent $CO_2$ accumulation and, where required, prevent asphyxiation.

Figure 2:
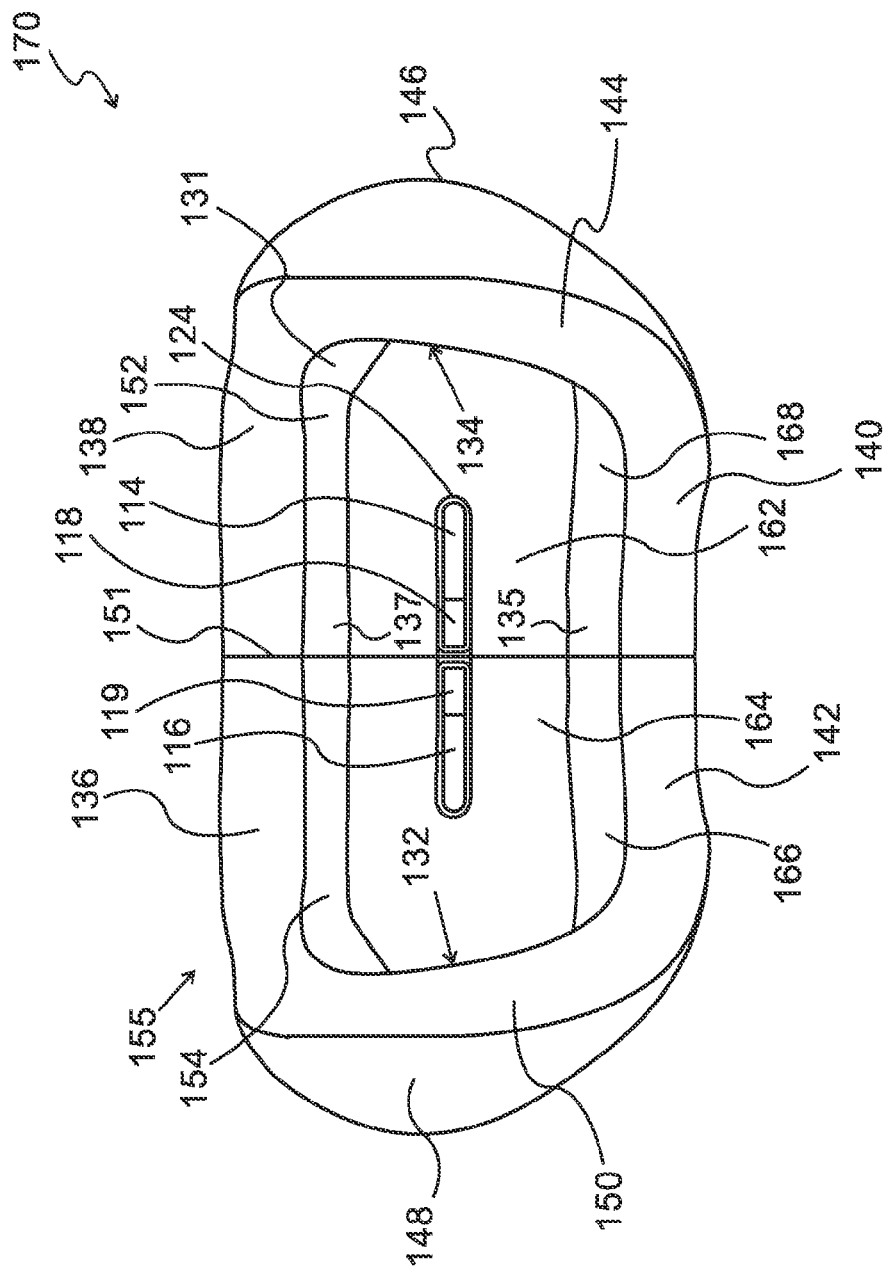

Interface 100 allows CPAP air or other gases to be delivered through tube section 120. Exhaled gases are discharged from the tube section via aperture 220 (and in a small number of cases, some of it may exit through the patient's nostrils). Aperture 220 comprises two slits 114, 116 (seen in FIG. 2). Slits 114, 116 are smaller in dimension than corresponding slits 118, 119 in an orifice 124 inside the interface (FIG. 2)

According to some embodiments, the patient is also provided with nostril bungs or stoppers to prevent exhaled air from escaping via the nostrils.

In preliminary experiments, we have found that the CPAP systems with interface 100 of the present invention allow for an air pressure of around 20-60% less than the requirements of all prior art interfaces. Prior art interfaces known in the art typically require air pressures in the range of in the range of 4-20 cm $H_2O$, depending on the patient. Thus the interfaces of the present invention provide similar or better therapeutic results using less air pressure.

Some of the problems associated with prior art interfaces includes that they are heavy, cumbersome and are generally uncomfortable. In sharp contrast, the interfaces of the present invention are:

a) much lighter, thinner in vertical cross-section and do not significantly weigh down on the gums and lips within the mouth, in comparison with the interfaces of WO08041237;

b) comprise a lingual rim which is constructed and configured to form circumferential hollow lip of the interface, wherein the hollow lip is adapted to bulge upon receiving air, thereby forming a circumferential air pocket within the circumferential hollow lip;

c) do not press down on any part of the tongue, does not touch the tongue or soft palate and does not protrude into the oral cavity lingual to the teeth leading to a hyperactive gag reflex;

d) do not press down on any part of the skin and lips externally to the oral cavity; and e) Self adaptable to the physical intra oral structure of each user.

Additionally, retainer elements loops 706 and 708 (FIG. 7A) for the interface, are connected to elements 206 and 208, are simpler and lighter than the retainer elements of the prior art interfaces. The retainer elements do not restrict head motion of the patient during sleep. Furthermore, retainer elements may not be required by many of the patients.

Figure 3:
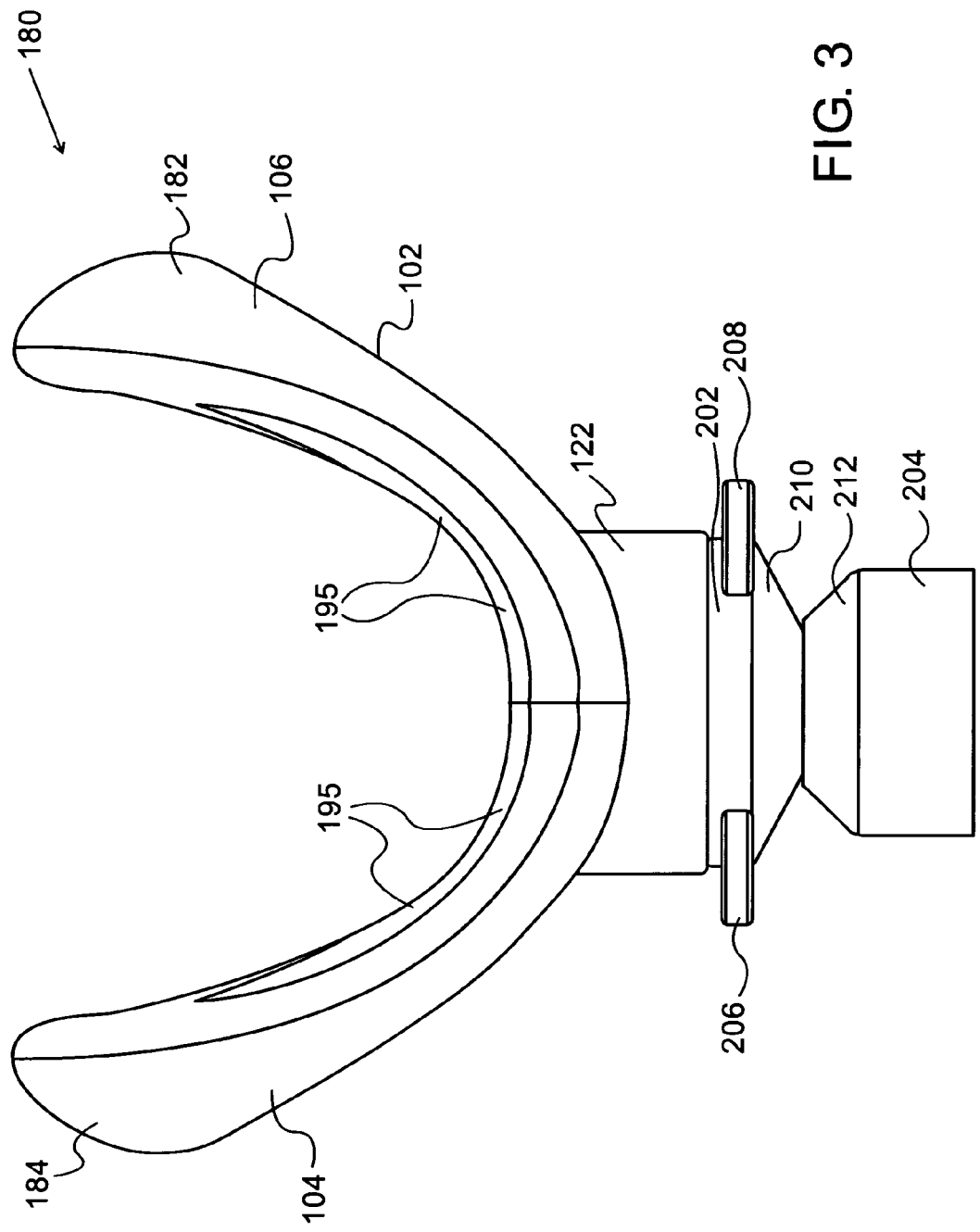
Figure 4:
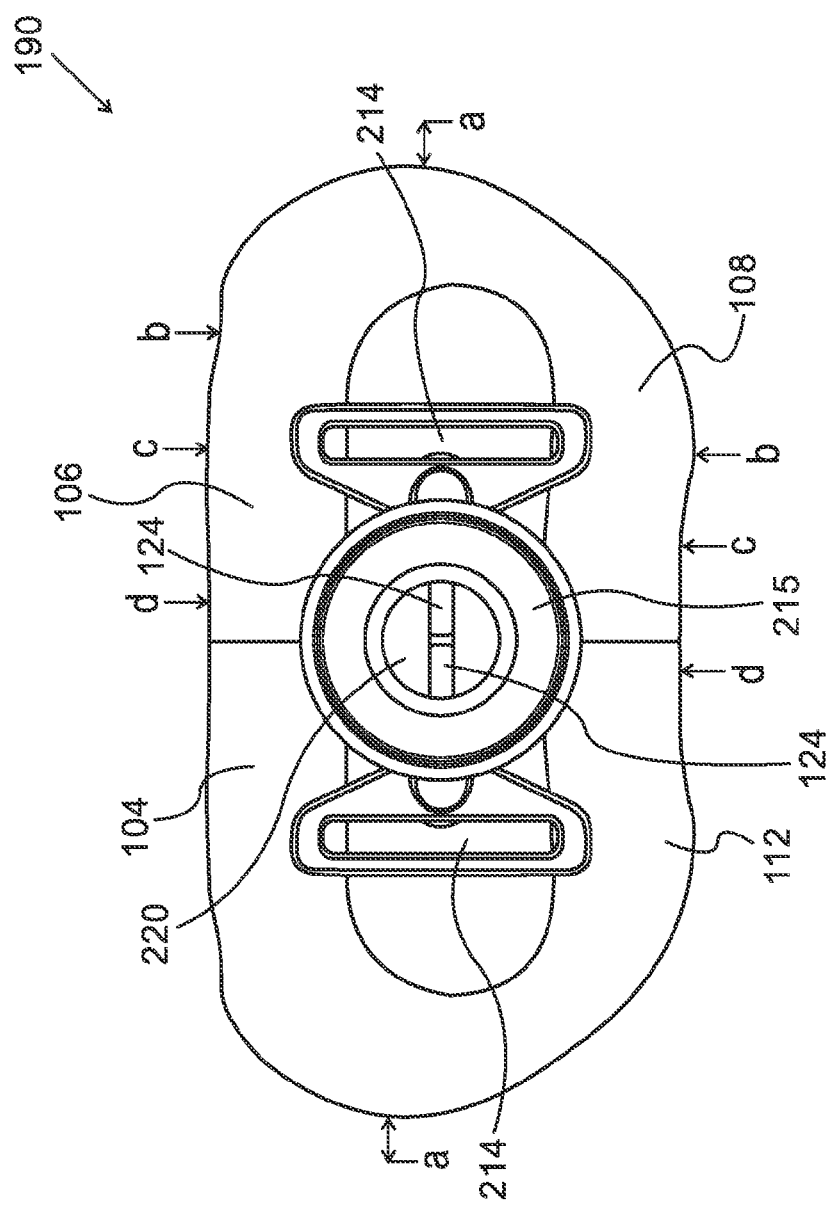

Reference is now made to interface 100 and further to FIGS. 2-4, which are simplified pictorial illustrations of a rear view 170, upper view 180 and front view 190 of the CPAP intra-oral interface of FIG. 1, respectively.

The interface typically weighs less than one hundred grams. In some cases, the interface weighs between 30-60 grams.

The interface may be suited for an adult or child. For adults, the interface may be constructed in a number of standardized sizes.

Some examples of the external dimensions of the interface are seen in Table 1 hereinbelow.

TABLE 1

Exemplary dimensions of the CPAP interface in accordance with one embodiment of the present invention (See FIG. 4)

| DIMENSION [cm] | Small adult | Medium adult | Large adult | child |
|---|---|---|---|---|
| WIDTH a-a | 11 | 13 | 15 | 9 |
| HEIGHT d-d | 2-2.5 | 2.5-3 | 2.5-3.5 | 1.5-2 |
| Height c-c | 3 | 3.5 | 4 | 2-3 |
| Height b-b | 2.5 | 3 | 3.5 | 2-2.5 |
| Aperture size [cm2] | 5-7 | 5-7 | 5-7 | 5-7 |

Interface 100 is typically made of a self-adaptable flexible biocompatible material 102, such as silicon. The hollowed ellipsoid tube is made of relatively soft self adaptable materials such as silicone. The interface is self-collapsible, as is described further with reference to FIGS. 6A-6B and FIG. 10 hereinbelow.

The hollowed ellipsoid tube section 120 is connected perpendicularly at an intra-oral end to two thin central sections 113, 115, disposed respectively to the left and right of a central vertical axis 151. Surrounding the central sections are four buccal bulging portions, namely an upper right buccal portion 104, an upper left buccal portion 106, a lower left buccal portion 108 and a lower right buccal portion 112. At each distal part of the interface, there is a hollow section which acts as a collector of air. It comprises thicker silicon lips and occupies the space adjacent to the posterior teeth.

As can be seen in FIG. 2, the interface comprises an inner rim 155, which is made of a thin layer of polymeric material (thinner than the outer rim). The rim may be of variable thickness, such as 0.5-2 mm. Rim 155 comprises a number of lingual portions, namely, a left upper portion 136, a right upper portion 138, a right lower portion 140, a left lower portion 142, a right side portion 144, and a left side portion 150. Portions 144, 150 are relatively wider than portions 136, 138, 140, 142, and additionally have a thicker cross section. The spaces formed by portions 144 and 150 are adapted to trap more exhaled air than portions 136, 138, 140, 142, wherein the distal portion is also wider buco-lingually, to form a larger air pocket than that formed at more proximal parts. This allows for a better seal at the posterior portions of the interface. These thicker portions create the required valve seal in this specific area of the mouth by gently pushing the mucosa over the buccinator muscle in an outward buccal direction. An inner surface 152 of upper right buccal portion 104, and an inner surface 154 of upper left buccal portion 106 are seen below left upper portion 136 and right upper portion 138. Similarly, FIG. 2 shows inner portions 166, 168 of the lower left and right buccal portions.

Reference is now made to FIG. 4, which is a simplified pictorial illustration of a front view 120 of a CPAP intra-oral interface of FIG. 1, in conjunction with FIGS. 1-3. Interface 100 comprises two orifices 214 for receiving retainer element loops 706 and 708 (see FIG. 7A hereinbelow). Adapter element 200 further comprises an inner annular surface for receiving and holding a conduit (not shown) connected to a gas supply.

Turning back to FIG. 2, rim 155 is symmetric about a vertical axis 151. The vertical axis may, according to some embodiments, also be a seal line formed during a molding process in the production of the interface. According to some embodiments, the rim extends 5-30% of the height d-d of the interface from each side thereof. In some cases, the rim is 10-20% of the height of the interface. The rim is constructed and configured to provide a circumferential air pocket (or air trap) 131 within the interface. Air pocket 131 comprises a left side air pocket 132 and a right sided air pocket 134, an upper air pocket 137 and a lower air pocket 135 with a lingual side open to collect exhaled air.

In one manifestation embodiment of this invention, the projections 101 and 103 can be duplicated towards the lips in addition to their position in interface 100.

As can be seen in FIG. 1, the circumferential air pocket inflates projections 101 and 103, thereby forming hollow "lips" around the interface.

The interface is seal forming, being in a first closed position as shown in FIG. 6A and in an open position, as is seen in FIG. 6B. When opened by the introduction of exhaled air, inner flaps push the lips away from the gums thereby forming a peripheral valve seal.

The interface is both lightweight and comfortable to touch.

Upon entry of inhaled air from the CPAP interface, air is sucked into rim 155 of intra-oral section 110, thereby forming air pockets 132, 134, 135 and 137. Intra-oral section 110 comprises a number of buccal portions 104, 106, 108, 112 (FIG. 1) on a front side, which are disposed buccally in the buccal sulcus and lingual portions 136, 138, 140, 142, 144, 150, as well as two side portions 146, 148 (FIG. 2).

The interface forms a seal 649 by means of undercuts 21, 634 (FIG. 6A) under the interface and is well gripped by the orbicularis oris on an outer (buccal) side thereof and by the gums and teeth on an inner (lingual) side thereof.

Reference is now made to FIG. 3, which is a simplified pictorial illustration of an upper view 180 of the CPAP intra-oral interface of FIG. 1. As can be seen in FIG. 3, the interface made of self-adaptable flexible biocompatible material 102 forms two symmetrical bulging hollowed portions 182, 184, formed at the ends of upper right buccal portion 104 and upper left buccal portion 106, respectively. Similar symmetric lower bulging portions are present too (not shown). There can also be seen an upper view of two welded connectors 210, 212 of adapter element 200.

Figure 5:
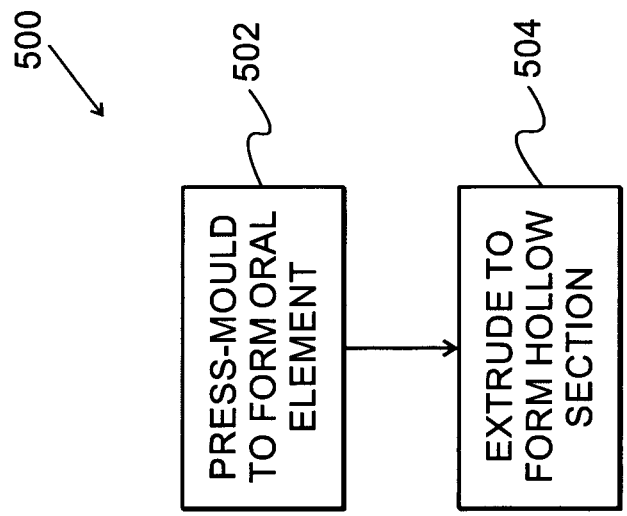

Reference is now made to FIG. 5, which is a simplified flow chart 500 of a method for forming a CPAP intra-oral interface, in accordance with an embodiment of the present invention. Prior to forming the interface, a patient's mouth internal dimensions are measured and classified in accordance with Table 1, hereinabove. For example, if the patient is classified as a medium adult, a mold is chosen which will form an interface matching the dimensions of a medium adult interface.

In a press-molding step 502, approximately 30-60 grams of a suitable biocompatible polymer are introduced into the "medium-adult" mold (not shown). The mold typically comprises two metallic symmetric sections with hollowed portions, as is known in the art. The metallic sections are pressed together under suitable pressure and temperature conditions thereby forming an oral element. The oral element is similar to the intra-oral element 110 of FIG. 1, but lacks tube section 120. Sections 113 and 115 meet along a continuous vertical axis.

In an extrusion step 504, a metallic bar is forced horizontally through sections 113 and 115, thereby forming tube section 120. Inner surfaces 164, 162 of sections 113, 115 are seen in FIG. 2.

There may be some optional further finishing steps, as are known in the art.

Reference is now made to FIG. 6A, which is a simplified pictorial illustration of a vertical cross section 600 of the CPAP intra-oral interface of FIG. 1 during inhalation, in accordance with an embodiment of the present invention As can be seen in FIG. 6B, there is shown a simplified pictorial illustration of a vertical cross section of the CPAP intra-oral interface of FIG. 1, during exhalation with air introduction, in accordance with an embodiment of the present invention.

FIGS. 6A-6B illustrate the generation of a valve seal when an optimally shaped interface 100 is placed in, and completely fills, the buccal sulci. Due to the presence of oral mucosa and a thin film of saliva 631 on the lingual surface of lips 630 and 635, the interfacial surface tension between the oral mucosa and the interface resists separation of interface 100 from the buccal sulci. A hermetic seal that secludes oral cavity 622 from outside air A is consequently generated, thereby allowing the air pressure within oral cavity 622 lingual to the teeth to increase. CPAP air can be therefore introduced to oral cavity 622 via adapter element 200; however pressurized air within oral cavity 622 is prevented from escaping via a buccal sulcus and atmospheric pressure air A is prevented from infiltrating to oral cavity 622 through a buccal sulcus by utilizing the phenomenon of the valve seal.

TABLE 2

Exemplary dimensions of the distances and angles in three different states of the CPAP interface for a medium adult in accordance with one embodiment of the present invention (See FIGS. 6A-6B and FIG. 10)

| DIMENSION [mm] | FIG. 6A (closed) | FIG. 6B (inflated) |
|---|---|---|
| Distance d | 0-3 mm | 2-7 mm |
| Angle φ | 0-10 | 5-30 |

Before the interface is introduced into the mouth, there is an angle of around 20-30 degrees formed between non-flexible portions 1004 and collapsible portion (loops) 1006 (see FIG. 10 hereinbelow), for example.

When the interface is introduced into the mouth, the loop is gently forced backwards against the gum. The gums are anterior to the interface. It should be understood that this is a symmetrical effect both to the upper and lower, left and right gums.

a) Preloading is effected by the interface being introduced into the mouth.

The seal formation is performed by the interface in two ways: active and passive.

b) The passive action is effected by the interface being present inside the mouth and occupies the potential space between the lips and gums.

The passive action includes a gentle spring-like action which exerts a preloaded force, which is inherent to the geometry of the rim to the inner-side of the lips, thereby creating the required seal (peripheral valve seal).

The buccal bulge or outer lower part of the rim forms a tissue undercut by pushing buccally the lips that are below and above the orbicularis oris, the circular muscle that forms the lips, The same action is performed by the side portions-seal is formed by pushing buccally the inner cheeks and the weak buccinator muscle which comprises the cheek walls.

c) The active seal is formed during exhalation. During inhalation, the passively formed seal suffices. In contrast, during exhalation, the air is forced out through the hollowed ellipsoid part and, at the same time, to the inner part of the rim and inflates and opens it. By doing so, it strengthens the seal, when it is most needed.

In clinical trials conducted with an intra-oral CPAP interface based on the embodiment of this invention, the CPAP treatment achieved the needed therapeutic results, while requiring reduced air pressure in comparison to the following interfaces: Comfort Gel size M by Respironics, Comfort Classic size S by Respironics, Comfort Classic size M by Respironics and Ultra Mirage by ResMed. The results are provided in Table 3.

TABLE 3

EXAMPLARY COMPARISON OF PERFORMANCE OF PRIOR ART CPAP INTERFACE WITH THE CPAP INTERFACE OF FIG. 1.

| Patient | Air pressure recorded with an exemplary embodiment of this invention's intra-oral CPAP interface (FIG. 1 cm H₂O | Air pressure recorded with a prior art CPAP interface (different from this invention intra-oral CPAP interface embodiment) cm H₂O | % of Reduction in required air pressure for achieving the therapeutic goal |
| --- | --- | --- | --- |
| Patient 1 | 7 | 13 | 46% |
| Patient 2 | 5 | 7 | 29% |
| Patient 3 | 5 | 7 | 29% |
| Patient 4 | 7 | 13 | 46% |
| Patient 5 | 5 | 6 | 17% |

It is easily understood from the above table that the present invention provides an intra-oral CPAP interface, which allow for much less air pressure than existing CPAP interfaces.

Therefore, the present invention provides an intra-oral CPAP interface, which allow for less air pressure in PAP treatment in order to achieve the same therapeutic results when compared to other existing CPAP interfaces.

Another interface embodiment consists only of the ellipsoid tube section 120 without the two thin central sections 113, 115. Surrounding the central sections are four buccal bulging portions, namely an upper left buccal portion 104, an upper right buccal portion 106, a lower right buccal portion 108 and a lower left buccal portion 112. It comprises thicker silicon parts and occupies the space adjacent to the posterior teeth.

There is thus provided according to some further embodiments of the present invention, an intra-oral interface (as described above) that is not connected to a CPAP machine during CPAP treatment. The CPAP treatment is supplied via other nasal or ora-nasal interfaces and in such a case the air pressure needed for a successful therapy is reduced by 10-60% relative to an existing CPAP interface, while the intra oral interface in this embodiment support and augment the action of the existing CPAP interface.

Reference is now made to FIG. 7A, which is a simplified pictorial illustration of a perspective view 700 of a CPAP intra-oral interface 100 of FIG. 1 with a retainer 701, in accordance with an embodiment of the present invention. Preferably, the retainer is lightweight and made of a fabric or polymeric material.

Retainer 701 is attached to elements 206 and 208 via two corresponding retainer element loops 706 and 708. The length of a retainer strap 702 can be adjusted by means of two adjuster elements 704, 704. Adjuster elements 704 may be clasped by clasp 710 or any other suitable holding arrangement.

In another embodiment manifestation, retainer 701 can be comprised of 2 or more straps like 702.

FIG. 7B shows a number of views of the CPAP intra-oral interface 100 with the retainer element 701 of FIG. 7A, in accordance with an embodiment of the present invention.

Figure 8:
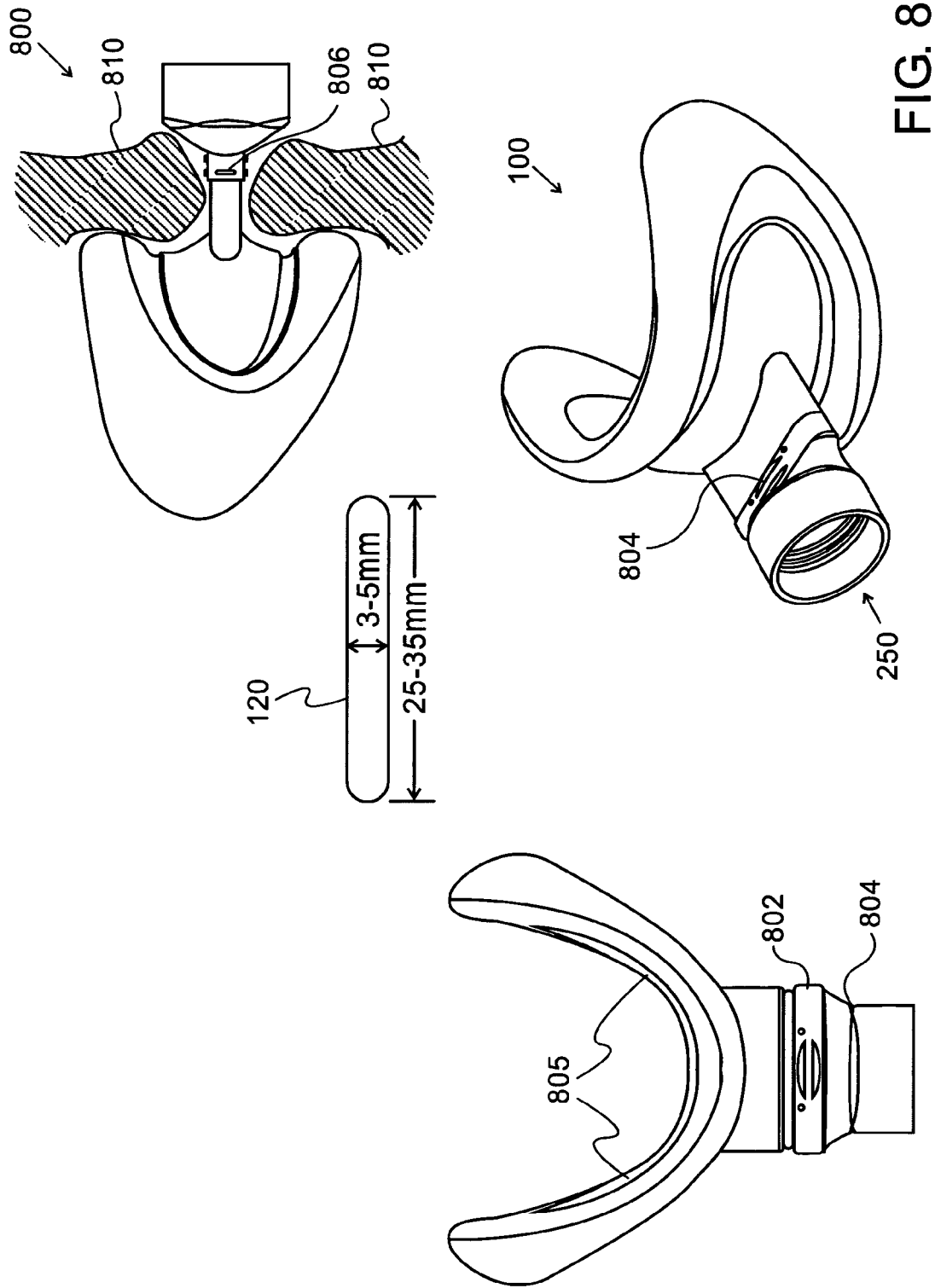

FIG. 8 shows a number of views of another embodiment of a CPAP intra-oral interface 800, in accordance with an embodiment of the present invention. Interface 800 differs from interface 100 in that it lacks elements 206, 208. Interface 800 comprises a connector element 802 comprising clips 804 which snap fit into adapter element 200 into the connector element. The connector element further comprises bulging elements 806. Connector element 802 connects between interface 800 and an air vent (not shown) adapted to introduce air 250 into the interface. The position of lips 810, relative to the interface is shown in the figure.

Tube section 120 (also seen in FIG. 1) typically has dimensions of 25-35 mm (length of flattened horizontal upper and lower sides 122) and a height of 3-5 mm.

FIG. 9 is a simplified schematic illustration of a dynamically adjustable CPAP intra-oral interface 900 comprising sets of pairs of coils, 901, 902 and 903, 904 designed to repulse each other, in accordance with an embodiment of the present invention. Interface 900 may be similar to interface 100 or interface 800.

In one embodiment of the invention, the distance between 901 and 902, and between 903 and 904 can be changed by fields and their resultant forces (e.g. by a magnetic field) or by a mechanical force (e.g. by a spring 913 and a connected piston 912), wherein the coils cause the active seal to expand and contract.

In a case wherein the distances between 901 and 902, and between 903 and 904 is caused by fields' resultant forces, then there will be two elements such as elements that creates magnetic field (e.g. coils) located near the top of the interface on both sides of lips of the rim such that 901 will be in the part closer to the lips from the inner side of the rim, 902 will be in the part closer to the teeth from the inner side of the rim and other two elements such as elements which create a magnetic field (e.g. coils) located near the bottom of the interface on both sides of lips of the rim such that 903 will be in the part closer to the lips from the inner side of the rim, and coil 904 will be in the part closer to the teeth from the inner side of the rim.

It is possible that the elements which creates magnetic field will be within the walls of the interface.

The elements which creates magnetic field will not impinge on tissues.

When an electric current flows in a certain direction through 901 and, in the same direction through 902, and at the same time, an electric current flows through element 903 and in the same direction through 904 respectively, then there will be repulsion between 901 and 902 and repulsion between 903 and 904 respectively.

The field intensity depends on the electric current intensity, number of coils, their geometry and their spatial structure.

It is possible that the coils in 901, 902, 903 and 904 will each be segmented into several independent coils so that each of 901, 902, 903 and 904 will be constructed of several sub coils and each such sub coil may receive electric current with different current intensity and direction from the other sub coils. This combination of sub coils with different electric currents will create segmented repulsion or attraction forces that will change accordingly the distances between sub segments of 901 and 902 and between sub segments of 903 and 904. This will allow a better fit of the interface to its user.

A suitable electric current source may be, for example, a battery 907 located outside the interface, such as in the air vent or hose or flow generator.

Alternatively the electric current source can be an alternate current source that is connected to the flow generator or completely external to the CPAP system. This alternate electric source may require use of a transformer (not shown).

Alternatively, fixed magnets (not shown) may be installed in 901, 902, 903 and 904 where the magnetic poles of 901 and 902 will be placed in a way that 901 and 902 will repulse each other and the magnetic poles of 903 and 904 will be placed in a way that 903 and 904 will repulse each other. This means that each pair 901-902 and 903-904 will have the same poles.

The strength of repulsion between elements that creates magnetic field can be fixed or variable.

If the strength of repulsion between elements that creates magnetic field is constant, then it must correspond with the air pressure the flow generator must supply, in a way that the strength of repulsion between elements that creates magnetic field will be sufficient to help the interface achieve a sufficient seal that will stops sleep apneas and hypopneas.

In a case wherein the strength of repulsion between elements that creates magnetic field power varies, this embodiment comprises the following additional components: One or more sensors 905, which can be placed on the central side of the interface, which faces the teeth near the interface air entrance and or near the adapter element 200 and/or in the air vent and or in the air tube (not shown).

In some cases, the sensor need not register data connected to air flow, then the sensor (or part of the sensors) can be placed in proximity to the place where data must be measured (such as on a fingertip for pulse measurement or saturation of oxygen).

The sensors measure one or more of the following parameters: air pressure, air flow speed, oxygen saturation, carbon dioxide concentration, pulse rate, blood pressure, etc.

In addition to the sensors, there is a data processing unit 906 associated with interface 900, which receives the sensor's measurement data, stores and processes it, as is known in the art. Data processing unit 906 may be placed in the air tube (not shown) in the adapter element or within the flow generator unit (not shown). The active seal is configured to receive signals from the data processing unit correlated to the sensor output for causing the active seal to iteratively bulge and contract.

Depending on the sensors' received data, the processing unit will regulate the intensity and direction of the current supplied to the elements, which creates the magnetic field and thus controls the strength of repulsion between elements that creates magnetic field. This will result in a better therapeutic system. For instance, it will be possible to increase the repulsion forces and increase the distance between elements 901 and 902 and between elements 903 and 904 and thus supply better seal whenever the air pressure measured by the sensor drops to a value less than a predetermined minimum.

Additionally, it is possible to reduce the repulsion forces and decrease the distance between 901 and 902 and between 903 and 904 and thus supply a looser seal whenever the air pressure measured by the sensor reaches a predetermined maximal value. For instance, it will be possible to increase the repulsion forces and increase the distance between 901 and 902 and between 903 and 904 and thus supply better seal whenever the oxygen saturation measured by the sensor drops to a value less than a predetermined minimum.

In a case where the processing unit indicates that there may be soon be an incidence of a single apnea or hypopnea, sensed according to data from the processing unit received from sensors 905, then the processing unit will cause creation of repulsion forces and increase the distance between 901 and 902, and between 903 and 904 and thus supply better seal whenever it reaches the conclusion that an apnea or hypopnea is imminent. Once the system registers that an episode of apnea/hyponea/other is avoided, the system is constructed and configured to reduce or switch off the repulsion forces until the next event.

It is also possible to update the algorithms within the processing unit.

It is further also be possible to update the parameters used by the processing unit.

In case that the interface allows reduction of distances between elements 901 and 902 and between elements 903 and 904 below a certain level, then the interface or the air vent connected to the interface, must possess an anti asphyxiation valve system.

Elements 901, 902, 903, 904 are constructed and configured to be isolated from direct body contact. Elements 901 and 902 may be placed in a Faraday cage to prevent and or reduce radiation.

Additionally, elements 903 and 904 may be placed in a Faraday cage to prevent and or reduce radiation.

In another embodiment of this invention, the distances between elements 908 and 909, and between elements 910 and 911 is controlled by pistons 912 and springs 913.

It will be possible to adjust the pistons (lengthening or shortening) before usage of the interface and thus determine the distance between elements 908 and 909 and between elements 910 and 911.

Piston adjustment, the spring constant and spring length will ultimately determine the distance between elements 908 and 909 and between elements 910 and 911.

A dynamic mode is possible in this embodiment, if the pistons adjustment can be performed by a small electric motor (not shown) acting as part of the piston, providing this adjustment is effected by the processing unit 906 instructions after the processing unit receives data from sensors 905.

In one invention embodiment manifestation sensors 905 and or processing unit 906 can transmit their information to the flow generator. In this case the flow generator may use the information to regulate its own activities and work in concert with the interface in order to provide a better treatment for the user.

In one invention embodiment manifestation, device 900 is constructed and configured to stop snoring. In this embodiment, the device is not connected to an air vent. Once the processing unit concludes that the user is snoring, the processing unit activates coils 901, 902, 903, and 904 to effect a gentle pulsing pattern. This pulsing will not waken the snorer, but will encourage him to change position and thus stop snoring as his air intake improves.

In another embodiment of this invention, the space between elements 901 and 902 and between elements 903 and 904 is built in an open cell configuration and can be filled the air supplied by the flow generator.

The air supplied by the flow generator (not shown), in whole or in part always passes through the open interface structure, filling it, pressing the lips of the interface to their opposing tissues and thus creates a seal between the environment outside the patient and inside the oral cavity.

The open cell structure allows the air to leave the structure but always keep enough air with in the open cell structure to create the needed seal.

In another embodiment, the interface can include sensor 905, such as an integral pulse oximeter or CO-oximeter on the central part of the shield that faces the inner side of the lips. In this place, only a thin layer of cells separate the peripheral blood vessels from the reading diodes of the oximeter, while the built in geometry of the shield adheres—pushes the oximeter to the inner side of the lips to allow for accurate continuous reading.

Pulse oximeters are of critical importance in emergency medicine and are useful for patients with respiratory or cardiac problems as well as patients with sleep apnea or hypopnea.

The pulse oximeter can monitor patients' oxygenation. CO-oximeter measures more accurately $O_2$ and CO. When these measurements are done on OSA patients, they can provide important information with clinical value. Changes in $O_2$ and CO concentration may indicate need for increased air supply for OSA patients or indicate need for reduced air supply for OSA patients. Action influenced by the processor can occur either at the flow generator or the interface as described before.

This built-in pulse oximeter (to the interface) makes it unnecessary to connect a pulse oximeter to a patient's finger. It allows for continuous $O_2$—CO monitoring.

Reference is now made to FIG. 10, which is a simplified pictorial illustration of another CPAP intra-oral interface 1000, in accordance with an embodiment of the present invention.

Interface 1000 is symmetrical about a horizontal axis and comprises a thick inner portion 1004, a thin-walled collapsible portion 1002 and looped end portions 1006. End portions 1006 are tapered and comprise a wider portion 1005 adjacent to the collapsible portion and an extreme portion 1007 which is much narrower than the wider portion. The loop acts as an air trap/pocket adapted to collect exhaled air, thereby being configured to expand and contract according to the quantities of exhaled air.

End portions 1006 are tapered wider at wiper portion 1005 adjacent to the collapsible portion 1002 and are narrower moving away from the collapsible portion 1002.

Dashed line 1010 represents the position of interface 1000 forming air pockets (such as circumferential air pocket 131, FIG. 1 (seen in FIG. 2 as air pockets 132, 134, 135, 137) air pockets 195, FIG. 3 and air pockets 805 (FIG. 8)). During the manufacturing of interface 1000, looped end portions 1006 are preloaded and moved 2-8 mm towards the gums, illustrated as being along a vertical line 1012. When the interface is inserted into the mouth, the thin-walled collapsible portion 1002 collapses the interface looped end portions 1006 back to a position along vertical line 1010, thereby creating a light pressure on the gums and improves the seal in between the gums and interface.

FIG. 11 is a simplified pictorial illustration of a rear view of a CPAP intra-oral interface 1100, in accordance with an embodiment of the present invention. According to this embodiment, the interface comprises a "v" shaped upper cut-out 1102 having a depth of about four millimeters and a width of about 6 millimeters. The cut out is symmetric about vertical axis 151 and are on left upper portion 136 and right upper portion 138 (FIG. 2). Additionally, a lower cut out 1108 is disposed symmetrically about vertical axis 151 on right lower portion 140 and left lower portion 142 (FIG. 2). Lower cut out is about 2 millimeters in depth and 6 millimeters in width. Interface 1100 comprises a centrally disposed orifice slit 1113 having an upper edge 1110 and a lower edge 1112.

FIG. 12 is a simplified pictorial illustration of a filled CPAP intra-oral interface 1200, in accordance with an embodiment of the present invention. According to this embodiment, the interface has hollowed out conduits 1202, filled with material 1204 which is adapted to retain a predetermined shape.

This material is shaped prior to the interface usage and, once deployed, it creates a seal much like the seal created in the previously explained invention embodiments. An example of appropriate materials for filling the elements is any biocompatible viscoelastic material. In some embodiments, the material is a gel or a sponge.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A self-adaptable intra-oral continuous positive airway pressure (CPAP) interface comprising:
   a) a flexible polymeric tube section adapted to receive continuous positive airway pressure (CPAP) from a CPAP source via an adapter element, and for delivering positive air pressure to a mouth of a patient; and
   b) a flexible polymeric intra-oral section formed in one piece with said tube section, said intra-oral section being configured to reside buccally to the teeth in buccal sulci, said intra oral section comprising a centrally disposed aperture in fluid communication with said tube section, and a circumferential hollow rim configured to form at least one air pocket therein, said at least one air pocket arranged to bulge with exhaled air and contract as the patient inhales thereby changing at least one of a vertical dimension and a lateral dimension thereof so as to maintain constant tissue contact with said buccal sulci to provide sealing during both inhalation and exhalation of said patient.

2. The self-adaptable intra-oral interface of claim 1, wherein said circumferential hollow rim comprises four buccal bulging portions constructed and configured to be self-adaptable to a physical intra-oral structure of said patient and are further adapted to adhere to said buccal sulci.

3. The self-adaptable intra-oral interface of claim 2, wherein said buccal bulging portions are formed symmetrically around two central sections disposed respectively to the left and right of a central vertical axis of said intra-oral section.

4. The self-adaptable intra-oral interface of claim 3, wherein said tube secton has a generally elliptical cross section, said tube section connected perpendicularly at an intraoral end to said two central sections.

5. The self-adaptable intra-oral interface of claim 1, wherein said circumferential hollow rim comprises left and right arcuate projections of bilateral symmetry with respect to said tube section.

6. The self-adaptable intra-oral interface of claim 5, wherein said at least one air pocket comprises two symmetrical hollow portions, formed by said left and right arcuate projections.

7. The self-adaptable intra-oral interface of claim 1, wherein the intra-oral section is pre-tensioned so that when it is inserted in the mouth of the patient, said intra-oral section creates a loading force against at least the patient's gums, thereby sealing said intra-oral section to said gums.

8. The self-adaptable intra-oral interface of claim 1, further comprising:
   c) at least one sensor for detecting a physiological characteristic of the patient, and wherein the intra-oral section is configured to receive signals correlated to an output of said sensor for causing the intra-oral section to iteratively bulge and contract,
   wherein the intra-oral section includes at least one collapsible portion configured to reside in the buccal vestibulum of the patient, and wherein the intra-oral interface includes at least one coil for causing the at least one collapsible portion to expand and contract responsive to the received signals.

9. The self-adaptable intra-oral interface of claim 8, further comprising:
   d) a flow generator configured to provide air to the adapter element;
   e) an air inlet controller; and
   f) a data processing unit configured to receive signals from the sensor and to send said signals to the at least one coil and to further send signals to the air inlet controller.

10. The self-adaptable intra-oral interface of claim 1, wherein said interface is constructed and configured to supply sufficient air to the patient at an air pressure of 3-16 cm $H_2O$.

11. The self-adaptable intra oral interface of claim 1, wherein said interface weighs between 20 and 50 grams.

12. An intra-oral continuous positive airway pressure (CPAP) interface for introduction in the buccal vestibulum between teeth and inner part of lips and cheeks in a mouth of a patient, the interface comprising:
   a) a hollowed ellipsoid tube section which opens towards the teeth;
   b) an adapter element in communication with a source of positive air pressure at a first end of the hollowed ellipsoid tube section; and
   c) an intra-oral section extending perpendicularly from a second end of said hollowed ellipsoid tube section, the intra-oral section comprising:
      i. a central aperture in fluid communication with said hollowed ellipsoid tube section,
      ii. at least one buccal ellipsoid surface around said central aperture, and
      iii. a hollow lingual rim projecting from a circumferential border of said at least one buccal ellipsoid surface,
   wherein said hollow rim is adapted to bulge upon receiving exhaled air thereby forming at least one circumferential air pocket and to contract as the patient inhales, and
   wherein said intra-oral section is adapted to be inserted within buccal sulci occupying substantially the entire volume of a buccal sulcus potential space during patient inhalation and exhalation.

13. The intra-oral continuous positive airway pressure (CPAP) interface according to claim 12, wherein the intra-oral section is integrally formed with said hollowed ellipsoid tube section of a flexible biocompatible polymeric material.

14. The intra-oral continuous positive airway pressure (CPAP) interface according to claim 12, wherein said at least one buccal ellipsoid surface comprises right and left longitudinally extending projections adjoining, and of substantial bilateral symmetry with respect to, said central aperture, each of said projections having adjoining upper and lower regions and each of said regions having adjoining proximal and distal portions, wherein each of said projections is configured, when inserted within a buccal sulcus, in such a way so as to adhere to the oral mucosa.

15. A system for continuously providing a user with sufficient air, the system comprising:
   a) a CPAP interface according to claim 1;
   b) at least one set of coils disposed in said interface;
   c) at least one sensor adapted to receive data from an interface neighborhood;
   d) a flow generator unit adapted to provide air to the CPAP interface; and
   e) a data processing unit constructed and configured to:
      i. process and store said data, and
      ii. provide signals responsive to said data to at least one of said coils and said flow generator unit.

16. The system of claim 15, wherein said circumferential hollow rim has an outer side, and inner side, and an opening configured to face the teeth of the patient, the opening configured to receive air exhaled by the patient so as to thereby bulge said air pocket and thereby causing the hollow outer rim to seal on the outer side against the patient's mucosa lining and orbicularis oris, and to seal on the inner side against at least the patient's gums.

17. The system according to claim 15, wherein said system is adapted to prevent at least one of sleep apnea, snoring and hypopnea.

18. The system according to claim 15, wherein the sensor is selected from an integral pulse oximeter and a CO-oximeter.

19. The system according to claim 15, wherein the intra-oral section is adapted to be inserted into potential space of the buccal sulci, and wherein distal portions of said intra-oral section are thicker than an adjoining proximal portion and than a corresponding distal portion of the buccal sulcus potential space; and
   wherein the distal portion is also wider buco-lingually, thereby adapted to form a larger air pocket than that formed at more proximal parts of the interface.

* * * * *